United States Patent
Kelly

(10) Patent No.: US 7,780,596 B2
(45) Date of Patent: Aug. 24, 2010

(54) NON-INVASIVE HEALTH MONITOR

(75) Inventor: Craig A. Kelly, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 2071 days.

(21) Appl. No.: 10/687,230

(22) Filed: Oct. 16, 2003

(65) Prior Publication Data

US 2004/0087865 A1    May 6, 2004

Related U.S. Application Data

(60) Provisional application No. 60/419,300, filed on Oct. 17, 2002, provisional application No. 60/464,198, filed on Apr. 21, 2003.

(51) Int. Cl.
*A61B 8/00* (2006.01)
(52) U.S. Cl. ............... 600/437; 600/438; 600/450; 600/500; 607/17
(58) Field of Classification Search ........... 600/437, 600/438, 450, 500; 607/17
See application file for complete search history.

(56) References Cited

U.S. PATENT DOCUMENTS

| | | | |
|---|---|---|---|
| 3,483,860 A | 12/1969 | Namerow | |
| 3,796,208 A | 3/1974 | Bloice | |
| 3,875,929 A | 4/1975 | Grant | |
| 4,357,944 A | 11/1982 | Mauser et al. | |
| 4,513,748 A | 4/1985 | Nowogrodzki et al. | |
| 4,638,808 A | 1/1987 | Mawhinney | |
| 4,862,361 A * | 8/1989 | Gordon et al. | 600/450 |
| 4,991,585 A | 2/1991 | Mawhinney | |
| 5,760,687 A | 6/1998 | Cousy | |
| 5,785,654 A * | 7/1998 | Iinuma et al. | 600/441 |
| 5,840,028 A * | 11/1998 | Chubachi et al. | 600/437 |
| 6,198,394 B1 | 3/2001 | Jacobsen et al. | |
| 6,308,098 B1 * | 10/2001 | Meyer | 607/17 |
| 6,811,536 B2 * | 11/2004 | Sun et al. | 600/500 |

\* cited by examiner

*Primary Examiner*—Brian Casler
*Assistant Examiner*—James Kish
(74) *Attorney, Agent, or Firm*—Francis A. Cooch

(57) ABSTRACT

The time between heartbeats is measured over a series of such heartbeats. The time interval between two successive events is calculated and stored as a first array. The time difference between adjacent heartbeat intervals is also calculated from the first array and recorded as a differential array. The differential array is subjected to frequency analysis. First the differential array data is linearly interpolated to increase the number of data samples. The interpolated data is then subjected to a fast fourier transform (FFT) yielding a power spectrum. Characteristic frequency ranges are then integrated and the resulting frequency domain spectrum(s) are analyzed for dominant frequency characteristics.

23 Claims, 9 Drawing Sheets

DELTA RESPIRATION RATE VARIABILITY EVALUATION PROCESS

NON-INVASIVE HEALTH MONITOR

CROSS REFERENCE TO RELATED APPLICATIONS

This application is related to and claims the benefit of U.S. Provisional Patent Application Ser. No. 60/419,300, filed Oct. 17, 2002 entitled "Non-invasive Health Monitor" and U.S. Provisional Patent Application Ser. No. 60/464,198, filed Apr. 21, 2003 entitled "Method of Resolving Adjacent Normal-to-Normal Frequency Characteristics".

BACKGROUND

Conventional physiological monitoring relies on the so-called vital signs of heart rate, blood pressure, core temperature, respiration rate, and more recently oxygen saturation. Due to their long history and widespread familiarity, conventional vital signs are the parameters of choice in physiological monitoring. The parameters evaluated through the vital signs are highly regulated by the organism in order to maintain life. While average values for the vital signs are constrained within a relatively narrow range during normal life, vital sign dynamics can provide insight into regulatory failure or regulatory compensatory actions as underlying physiological challenges are addressed by the organism.

There is growing interest in monitoring additional parameters in an attempt to better define physiological status using easily measured indications. One such group of parameters is variability, e.g., arterial blood pressure variability, heart rate variability, QT interval variability, etc. Such parameters can be extracted from high precision vital sign measurements. Current indications are that variability measures may provide a sensitive means of identifying physiological control indicators of challenges to homeostasis. Unfortunately, the interpretation of variability is complex due to challenges in effective parameterization.

SUMMARY

The evaluation of variability in heart period, arterial blood pressure, and electrocardiography (ECG) QT interval data is proving to be a powerful means of non-invasively monitoring autonomic nervous system activity as the body responds to varying actual or perceived stressors. However, conventional means of analysis have proven challenging to interpret under a variety of conditions relevant to telemedicine applications. Traditional means of monitoring variability involve evaluation of the time interval data of successive events in the frequency domain. The frequency spectrum, however, is dominated by very low frequency events that can obscure critical frequency bands in the 0.04 to 0.5 Hz region. This is especially the case for data acquired over short time intervals where the focus is on higher frequency information. To overcome this limitation we have found that the variance in time interval between two events, e.g., the time interval difference between adjacent heart beats (or interval delta), rather than the time interval itself, greatly simplifies interpretation of the variability data. Further, the use of interval delta measurements significantly improves the reliability of individual measurements in providing physiologically meaningful information for any heart rate measurement of sufficient time precision.

High time precision heart cycle timing is used for, inter alia, the evaluation of heart rate variability measurements previously achievable with sufficient precision through relatively cumbersome electrocardiography measurements. The present invention has further refined heart rate variability power spectrum analysis to suppress very low frequency (VLF) and ultra low frequency (ULF) components that reside below 0.04 Hz. The heart rate variability analysis described by the present invention and referred to as delta heart rate variability ($\Delta$HRV or DHRV) allows a clear representation and simplified assessment of the more physiologically established low frequency (LF) and high frequency (HF) components.

Physiological monitoring in, for example, emergency medicine, telemedicine, athlete monitoring, veterinary medicine, and clinical prescreening applications requires an effective means of acquiring physiologically relevant and easy to interpret information. Such applications require minimal invasiveness, maximal comfort to the subject, small dimensions, and high reliability. Further, the device must be easy to operate, i.e., it must effectively integrate physiological parameter sensor(s) with signal processing capable of condensing the acquired data to a meaningful and manageable form.

In order to develop a viable, simple, and robust physiological status monitoring system, the present invention utilizes a non-contact, through clothing, heart and respiration rate sensor that is amenable to miniaturization with sufficiently high time precision to allow for variability assessment. While microwave devices for measuring heart and lung motions have been extensively described in the literature, no report has provided evidence for sufficiently high time precision for a meaningful evaluation of variability other than ECG. Herein, a simple CW radar sensor is utilized to sense and detect skin surface motion and vibration. In one implementation, the apparatus utilizes an unmodulated CW 24 GHz radar with quadrature detection and high pass filtering of the sensed data. The filtering typically involves a 10 Hz, 12 dB/octave high pass filter and sampling at a rate of 1 kHz. Once the signals are collected the signal data is processed. Signal processing includes band pass filtering in the 10 to 150 Hz range for cardiac vibration signals, 0.5 to 15 Hz for cardiac motion signals, and 0.05 to 0.8 Hz range for respiration motion signals.

Evaluation of the frequency dependence of physiological variability such as heart rate variability is often rendered difficult because of a tailing baseline due to baseline offsets and/or oscillations that are outside of the frequency range of primary interest in the time domain data set under investigation. The process set forth herein is a simple yet powerful means of zeroing and stabilizing the time domain data set which provides a stable frequency domain baseline.

For cardiac analysis, the time between heartbeats is measured over a series of such heartbeats. The time interval between two successive events is calculated and stored as an array. The time difference between successive heartbeat intervals is also calculated and recorded as a delta array. The time difference can also be calculated for non-successive heartbeat intervals such as every other interval, every third interval, etc. The delta array is then subjected to frequency analysis. First the delta array data is linearly interpolated to increase the number of data samples. The interpolated data is then subjected to a fast Fourier transform (FFT) yielding a power spectrum. Characteristic frequency ranges are then integrated and the resulting frequency domain spectrum(s) are analyzed for dominant frequency characteristics.

DETAILED DESCRIPTION

Figure 1:
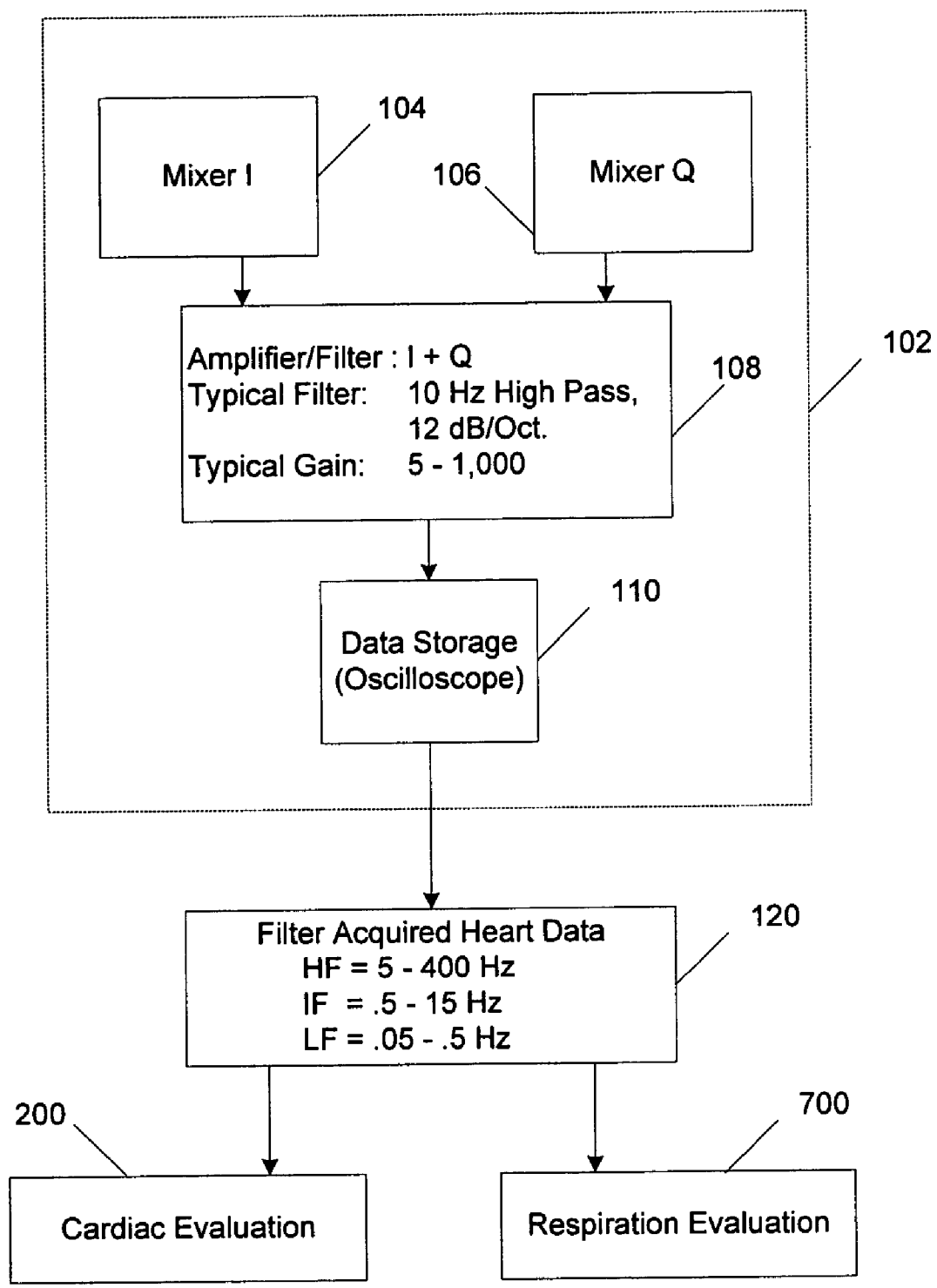
FIG. 1 is a block diagram of the top level functions of the present invention.

FIG. 1 is a block diagram of the present invention grouped by function. There are three primary functions involved with the present invention. The first function is a data gathering function 102. This function involves sensors and physical equipment not necessarily in contact with a subject for the purpose of acquiring heart vibration data. The current sensor is a CW Doppler radar (homodyne) operating between 24.12 and 24.13 GHz (K band). An output power of about 5 mW was used to feed a planar array microwave antenna. While the present invention can implement numerous antenna array configurations like a pyramidal horn or planar array antennas, the planar array allows for a more convenient sensor package. The power output from the antenna is directed approximately normal to the skin surface being probed through an air or other dielectric spacer (typically between 1 and 10 mm) and through clothing. The clothing can even include soft body armor. Compression of the antenna face against the skin surface has been found to suppress the signal intensity.

Radiation reflected off of the skin surface is collected by the antenna array and detected by both in-phase (I-channel) 104 and quadrature phase 106 (Q-channel, 90° out-of-phase) mixers. Currently, the signal output from both channels is summed and passed through a 10 Hz, 12 dB/octave, high-pass filter 108 prior to recording by a digital oscilloscope 110. The above ranges and values for the various components are illustrative in nature and not intended to limit the scope of the present invention. One of ordinary skill in the art can vary some or all of the values without departing from the spirit or scope of the present invention.

Stored data is then sent to a pre-filter 120 for further refinement into high frequency (HF) data, intermediate frequency (IF) data, and low frequency (LF) data. The approximate frequency ranges for the data are: HF~5 to 60 Hz; IF~0.5 to 15 Hz; and LF~0.05 to 0.5 Hz. There is some crossover between the HF and IF frequency ranges.

Figure 2:
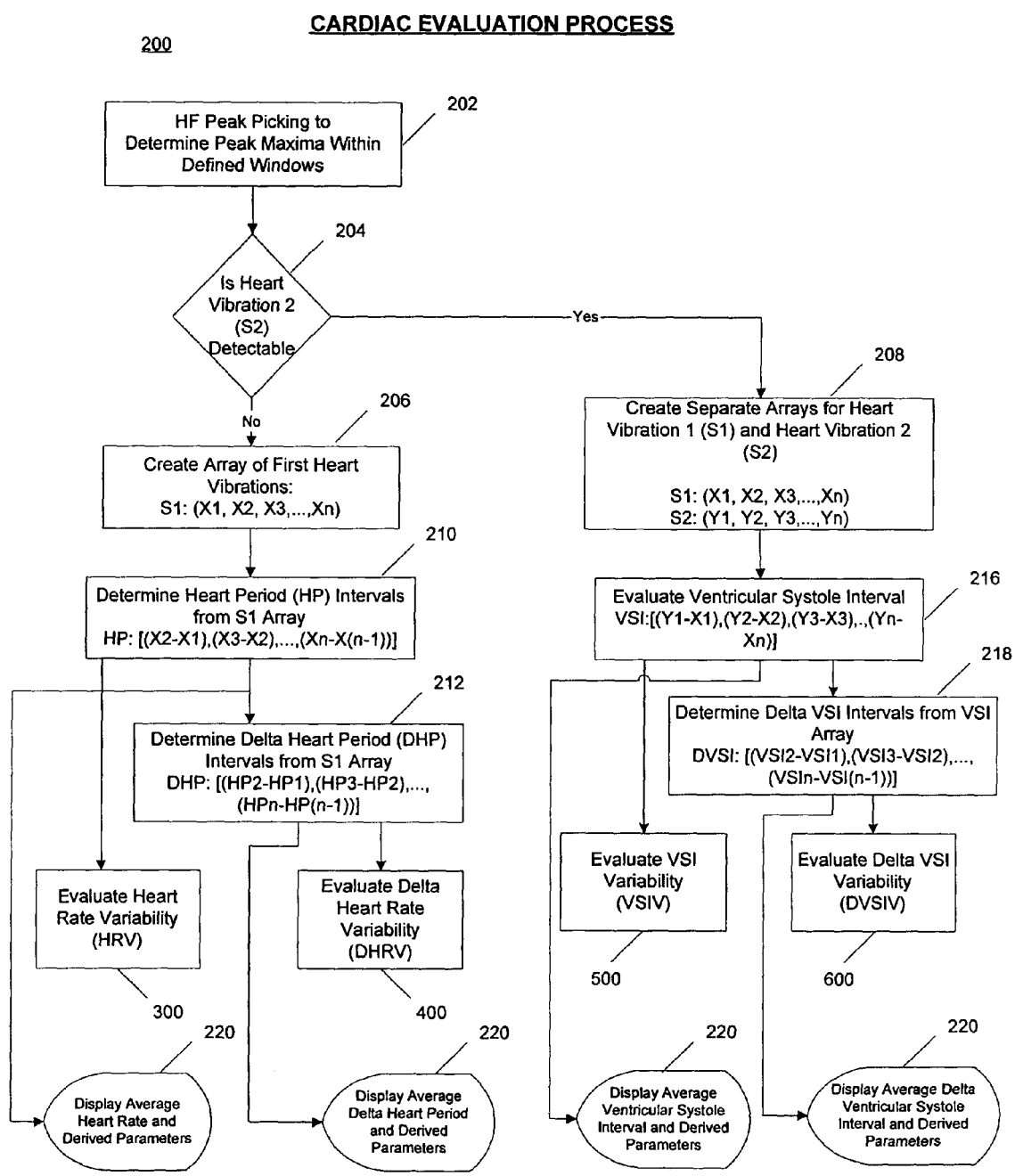
FIG. 2 is a top level data flow diagram of the cardiac evaluation process.

Filtered data is now ready for analysis and evaluation. There is a cardiac evaluation process 200 and a respiration evaluation process 700. FIG. 2 is a top level logic diagram illustrating the pre-processing steps performed on the pre-filtered data for cardiac evaluation.

The first sub-process is termed high frequency (HF) peak picking 202. Peak picking determines when the peak maxima of each heartbeat within a defined window of time. Decision block 204 determines whether a second heart vibration associated with each heartbeat is detectable. If it is not, then an array of the first heart vibrations, S1, is created in block 206. If the second heart vibration, S2, is detectable then a separate array of the second heart vibrations is also created in block 208.

For heart rate variability (HRV) analysis and delta heart rate variability (ΔHRV) analysis only the primary heart vibration array, S1, is required. First, an array of heart period (HP) intervals is created by taking the difference between successive elements of the S1 array. This is shown in box 210. The HP array provides the data required to perform a heart rate variability (HRV) evaluation process 300. To perform a delta heart rate variability (ΔHRV) evaluation process 400, the HP array is further processed to obtain a delta heart period (ΔHP) array. This is shown in box 212 where successive HP intervals determined from the S1 array are differenced to determine a ΔHP array. While successive HP intervals have been illustrated herein, other patterns of intervals can be implemented. For instance, every other HP interval can be differenced to create the ΔHP array. Or, every third HP interval can be differenced to create the ΔHP array. The ΔHP array is then passed to the process that evaluates delta heart rate variability (ΔHRV).

For ventricular systole interval variability (VSIV) analysis and delta ventricular systole interval variability (ΔVSIV) analysis both primary and secondary heart vibrations are needed. The primary heart vibration array, S1, has already been described in box 206. A secondary heart vibration array, S2, is created in box 208. The time period between the first and second heart vibrations of a single heartbeat is defined as the ventricular-systole interval (VSI). A VSI array is created by recording the VSI for each heartbeat. This is shown in box 216. Once this array has been calculated it can be further processed to evaluate VSI variability 500.

To evaluate delta ventricular systole interval variability (ΔVSIV), a ΔVSI array is created by recording the differences between successive (or non-successive) VSI values. A successive implementation is shown in box 218. The parameters derived from the various arrays as well as their average values can be displayed to a system operator as described in box 220.

Figure 3:
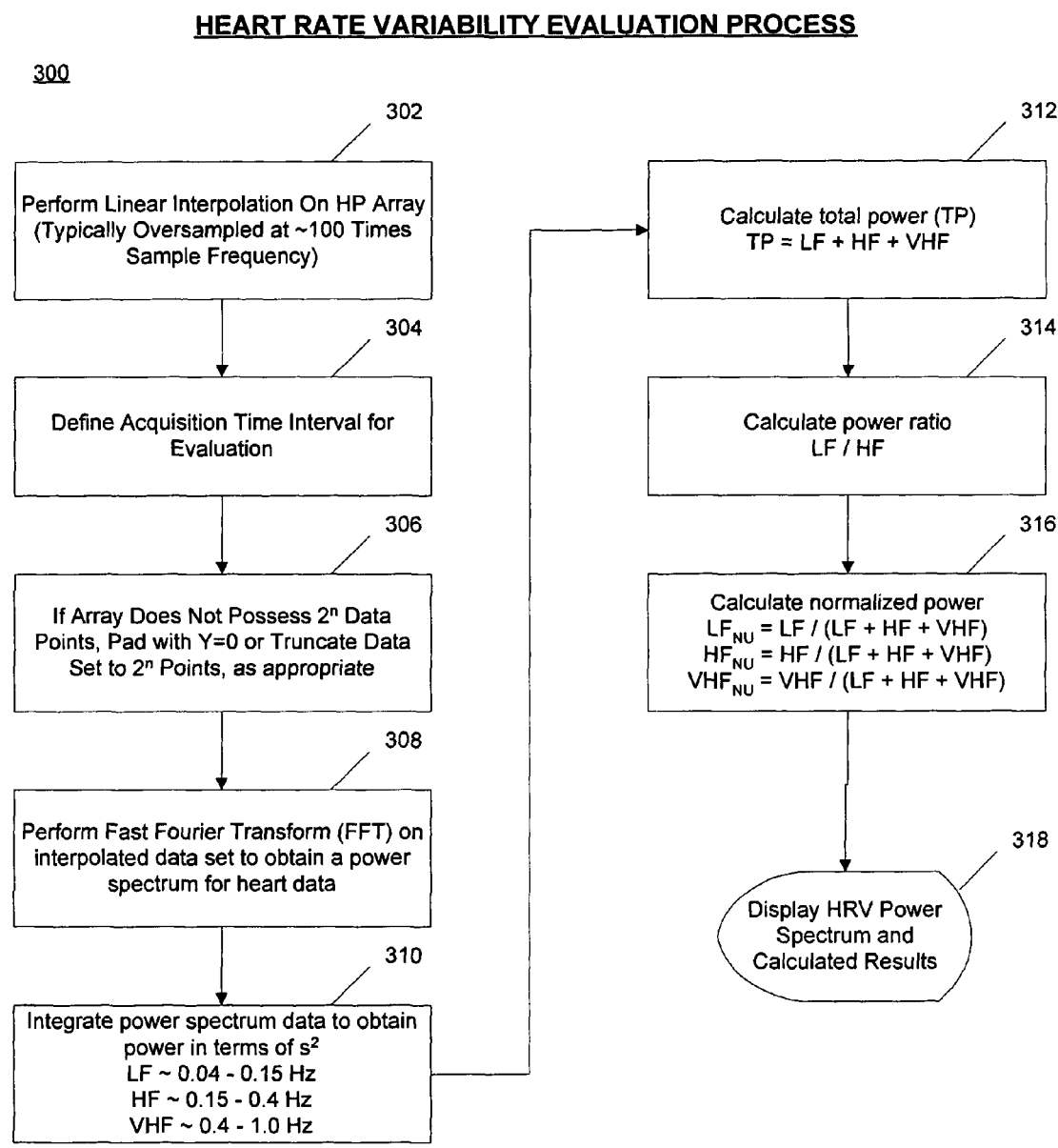
FIG. 3 is a data flow diagram of the heart rate variability (HRV) evaluation process.

FIG. 3 is a data flow diagram of the heart rate variability (HRV) evaluation process 300. This process uses as its input data the HP array recorded by box 210 of FIG. 2. The steps described in FIG. 3 apply to the other cardiac evaluation processes and will not be repeated for each different cardiac evaluation process. The differences among the cardiac processes of FIGS. 3-6 lie in the input data set that is acted upon. The input data sets are fully described by the procedures set out in FIG. 2.

Referring now to FIG. 3, the input data array is typically oversampled and linearly interpolated 302 to increase the number of data values for subsequent calculations. The system operator then defines a time interval, n, to be evaluated 304. The array is then set to 2n data points 306 by either padding the array or truncating the array as appropriate. The interpolated data set of 2n points is then subjected to a fast fourier transform (FFT) 308 to obtain a power spectrum for the heart data. This effectively converts the heart data from the time domain to the frequency domain for additional analysis. The power spectrum data is integrated 310 to obtain discrete power readings in terms of $s^2/Hz$. Low frequency (LF) readings are integrated between approximately 0.04 to 0.15 Hz. High frequency (HF) readings are integrated between approximately 0.15 to 0.4 Hz. Very High frequency (VHF) readings are integrated between approximately 0.4 to 1.0 Hz.

LF data analysis yields information pertaining to both the parasympathetic and sympathetic nervous system. The HF and VHF data analysis typically yields only information pertaining to the parasympathetic nervous system. The parasympathetic nervous system is known as the calming branch of the body's nervous system while the sympathetic nervous system controls during periods of stress.

The total power, TP, is calculated by summing the individual integrated LF, HF, and VHF values 312. A low to high power ratio of LF/HF is also calculated in box 314. Finally, normalized power values ($LF_{NU}$, $HF_{NU}$, $VHF_{NU}$) are calculated for each of the LF, HF, and VHF power values as shown in box 316. All of the power readings have an analytical value that pertains to the overall health of the individual from whose heart the data was obtained. Trained specialists can plot 318 and study the power data values to assist in identifying risk characteristics or other medical anomalies.

Figure 4:
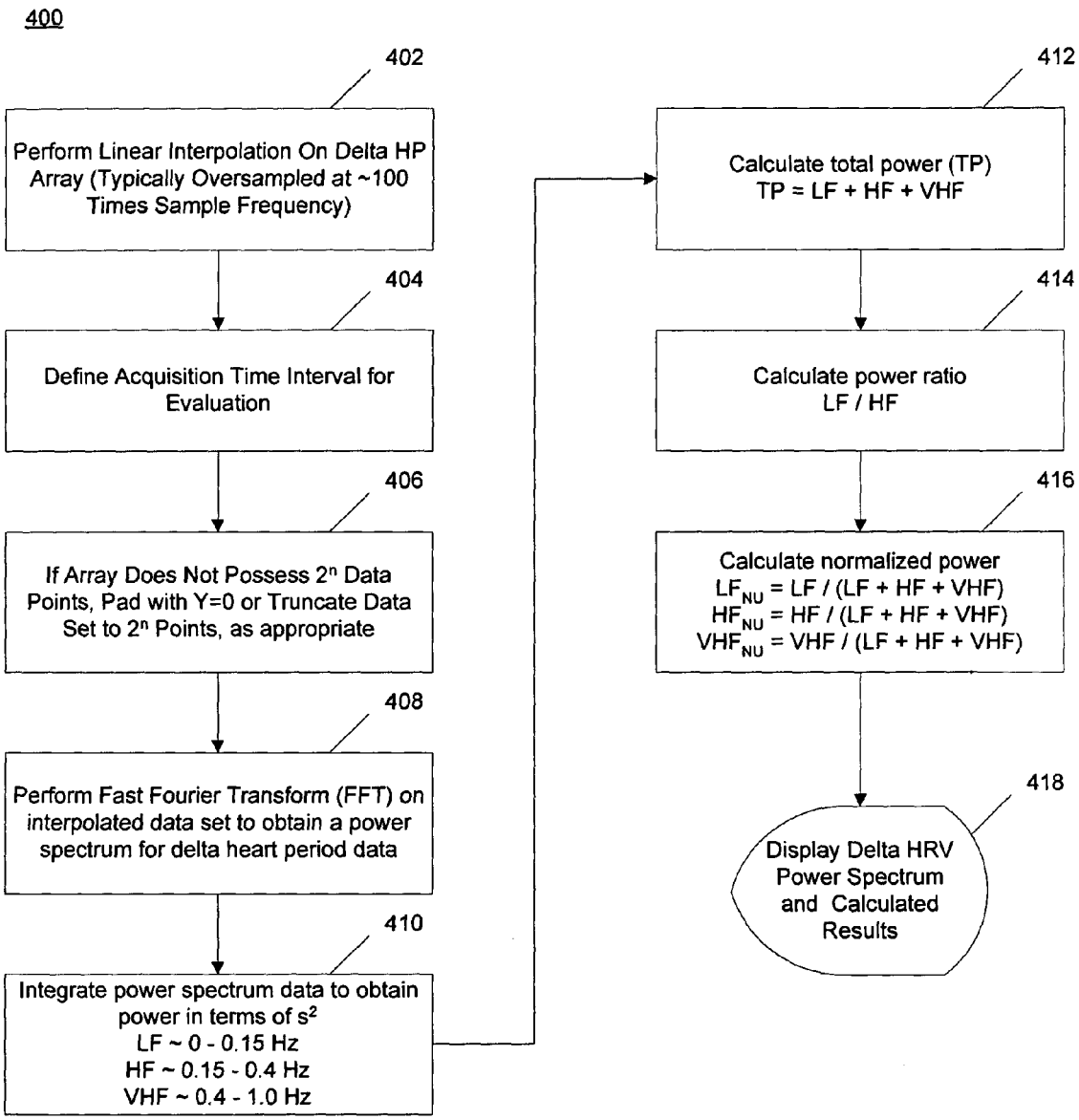
FIG. 4 is a data flow diagram of the delta heart rate variability (ΔHRV) evaluation process.

FIG. 4 is a data flow diagram of the delta heart rate variability (ΔHRV) evaluation process 400. This process uses as its input data the ΔHP array recorded by box 212 of FIG. 2. The process illustrated in FIG. 4 is identical to that of FIG. 3. The only difference is the original set of input heart data. Rather than using the heart period (HP) interval array, the ΔHRV evaluation process 400 uses the ΔHP array. The HRV analysis extracts information based on the interval between successive heartbeats while the ΔHRV analysis extracts information based on the power readings derived from the interval difference in adjacent heartbeats. Thus, while the mathematical manipulations of the input data set are the same, the input data set itself is different leading to additional inferences and conclusions regarding the original set of acquired heart data from box 120 of FIG. 1.

Figure 5:
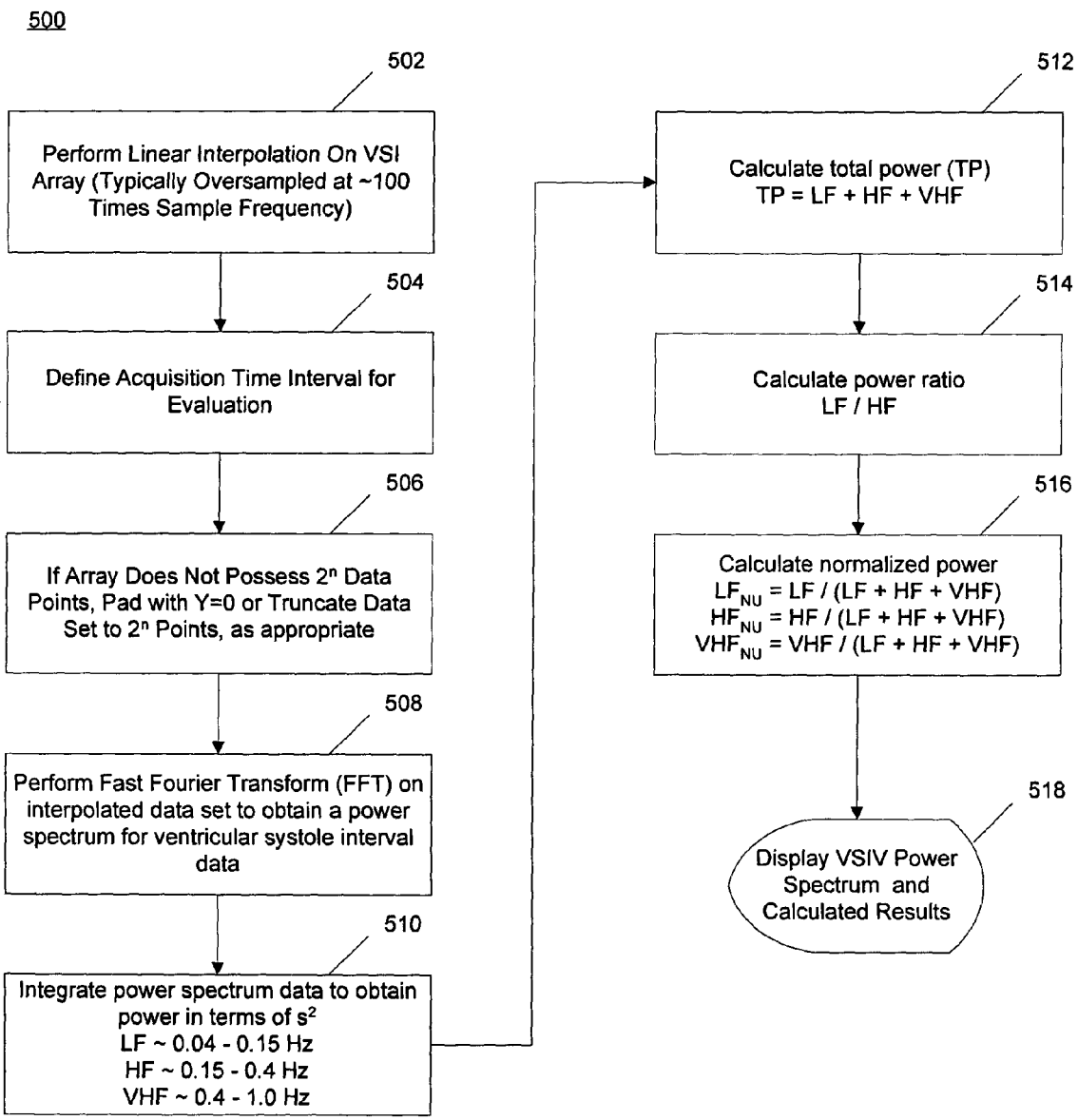
FIG. 5 is a data flow diagram of the ventricular systole interval variability (VSIV) evaluation process.

FIG. 5 is a data flow diagram of the ventricular systole interval variability (VSIV) evaluation process 500. The time interval between the first and second heart sounds defines the period of ventricular systole as defined by heart valve activity. The ventricular systole interval is related to the electrophysiological QT interval which represents the time interval of heart depolarization and repolarization. QT interval variability is a known phenomena attributed to autonomic control.

This process uses as its input data the VSI array recorded by box 216 of FIG. 2. Just as in FIG. 4 and FIG. 3 described above, the mathematical manipulations of the input data set for the VSIV analysis shown in FIG. 5 are the same. The VSIV analysis requires data for both the first and second heart vibrations, S1 and S2, associated with a heartbeat. The time difference between S1 and S2 for a given heartbeat is termed the ventricular systole interval (VSI). S1 is representative of the ventricular heart vibration and S2 is representative of the systole heart vibration. VSIV analysis extracts information based on the power readings derived from the S1/S2 interval difference of each heartbeat in the sample. Thus, while the mathematical manipulations of the input data set are the same, the input data set itself is different leading to additional inferences and conclusions regarding the original set of acquired heart data from box 120 of FIG. 1.

Figure 6:
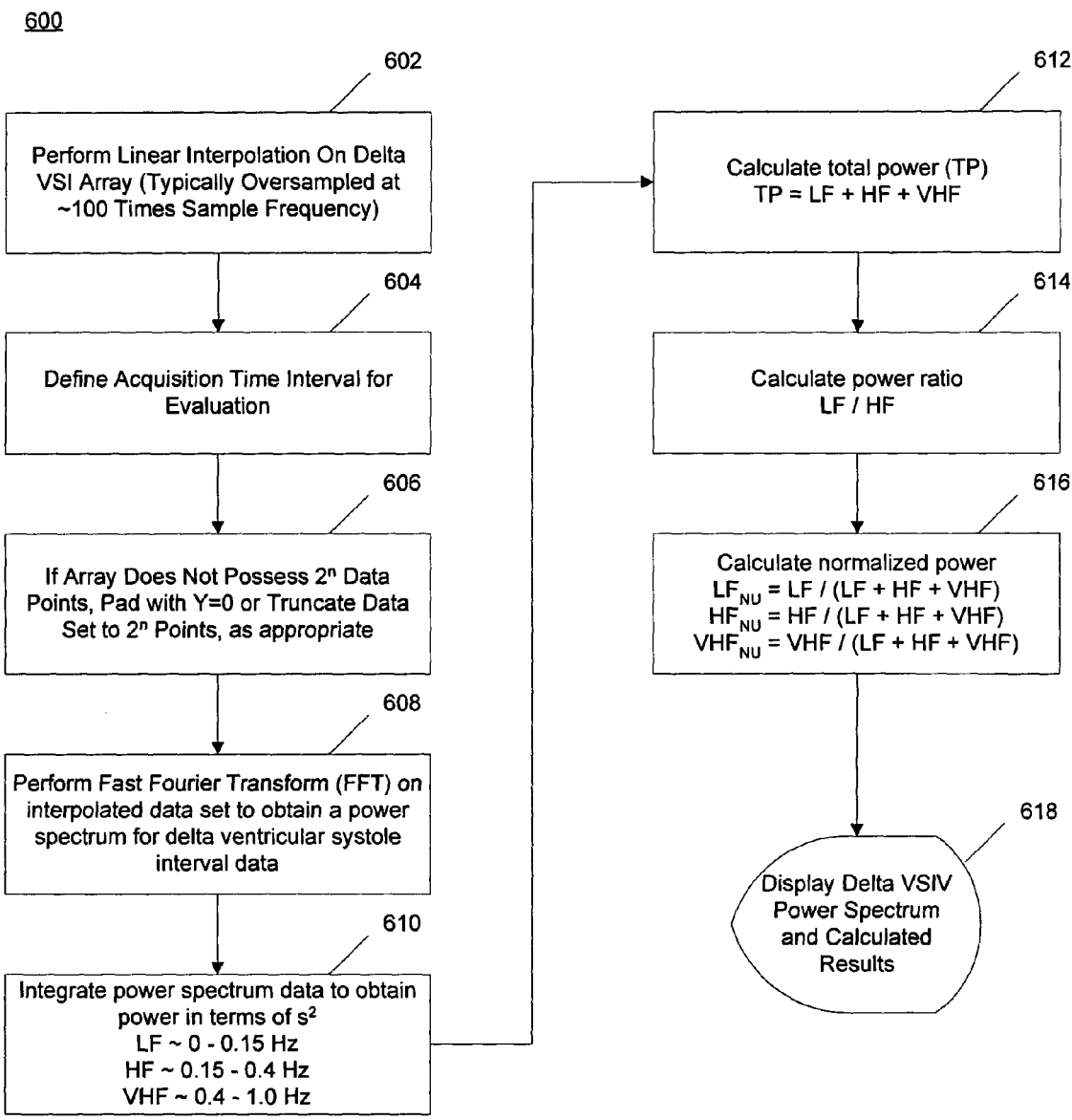
FIG. 6 is a data flow diagram of the delta ventricular systole interval variability (ΔVSIV) evaluation process.

FIG. 6 is a data flow diagram of the delta ventricular systole interval variability (ΔVSIV) evaluation process 600. This process uses as its input data the ΔVSI array recorded by box 218 of FIG. 2. Just as in FIGS. 3-5 described above, the mathematical manipulations of the input data set for the ΔVSIV analysis shown in FIG. 6 are the same. The ΔVSIV analysis also requires data for both the first and second heart vibrations, S1 and S2, associated with a heartbeat. ΔVSIV analysis extracts information based on the power readings derived by differencing the VSI of adjacent heartbeats in the sample. Thus, while the mathematical manipulations of the input data set are the same, the input data set itself is different leading to additional inferences and conclusions regarding the original set of acquired heart data from box 120 of FIG. 1.

The respiration period is not a constant, but rather oscillates in time. The frequency dependence of the respiration rate variability is difficult to quantify using conventional variability analysis methods, but is more clearly defined using delta variability analysis methods.

Figure 7:
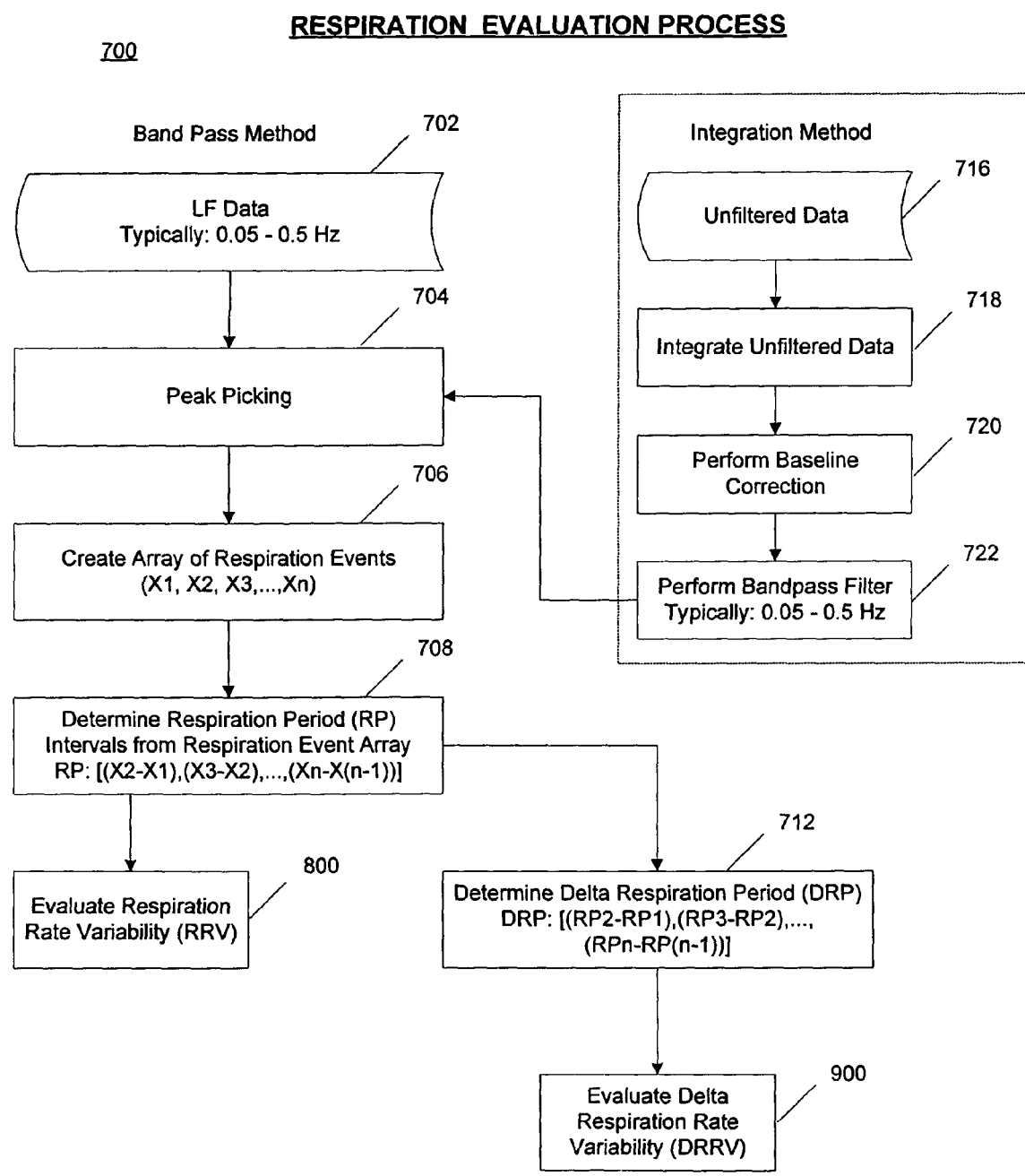
FIG. 7 is a top level data flow diagram of the respiration evaluation process.

FIG. 7 is a top level data flow diagram of the respiration evaluation process 700. The respiration evaluation process begins with the filtered heart sound data resulting from the manipulations illustrated in box 120 of FIG. 1. Respiration analysis focuses on the low frequency (LF) data set that is more closely correlated with respiration events rather than cardiac events. The raw LF data can be pre-processed using either a band pass methodology or an integration methodology. The band pass method limits the data set to a frequency range between 0.05 and 0.5 Hz 702. The integration method starts with unfiltered data 716 and integrates the unfiltered data 718. A baseline correction procedure 720 is performed on the integrated unfiltered data before it is baseline filtered 722 to exclude data not in the 0.05 to 0.5 Hz range.

Regardless of which pre-processing method is selected, the resulting 0.05 to 0.5 Hz LF data is subjected to a peak picking process 704 similar to that described in FIG. 2. This time the peak picking process 704 operates on the LF data rather than the HF data. Peak picking determines when the peak maxima of each respiration event within a defined window of time. The peak values are then organized into an array of respiration events as shown in box 706. The respiration event array is processed to create a respiration period (RP) array. This is illustrated in box 708 and involves determining the interval or difference between successive respiration events. This array provides the input for the respiration rate variability (RRV) process 800. An additional step is performed on the RP array to determine a ΔRP array 712. The ΔRP array is comprised of values representing the differences between successive RP intervals as opposed to the intervals themselves. The ΔRP array is then used to evaluate delta respiration rate variability ΔRRV 900.

Figure 8:
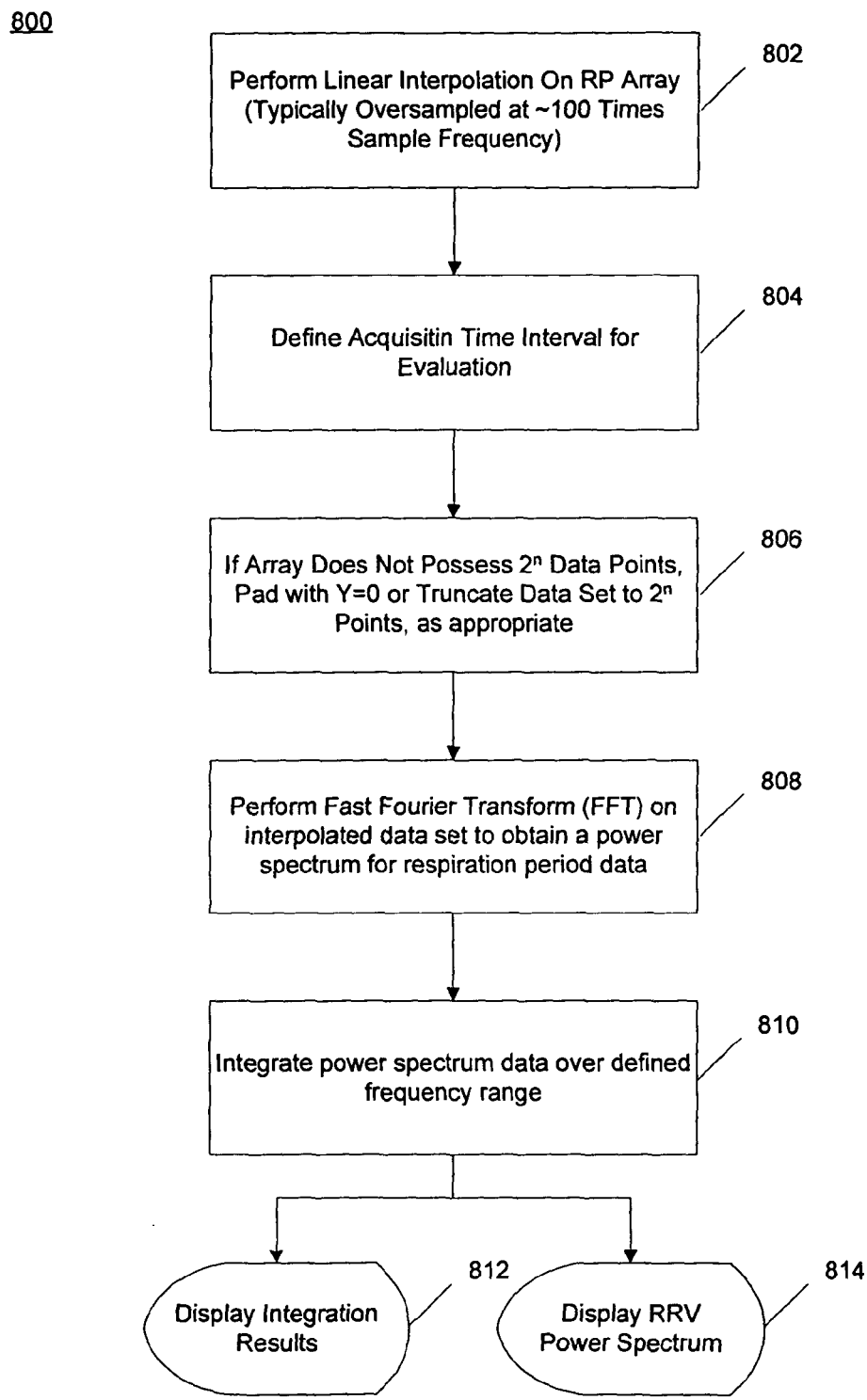
FIG. 8 is a data flow diagram of the respiration rate variability (RRV) evaluation process.

FIG. 8 is a data flow diagram of the respiration rate variability (RRV) evaluation process 800. This process uses as its input data the RP array recorded by box 708 of FIG. 7. The input data array is typically oversampled and linearly interpolated 802 to increase the number of data values for subsequent calculations. The system operator then defines a time interval, n, for evaluation 804. The array is then set to 2n data points 806 by either padding the array or truncating the array as appropriate. The interpolated data set of 2n points is then subjected to a fast fourier transform (FFT) 808 to obtain a power spectrum for the respiration event data. This effectively converts the respiration event data from the time domain to the frequency domain for additional analysis. The power spectrum data is integrated 810 between approximately 0.04 to 0.15 Hz to obtain LF power readings in terms of $s^2$/Hz. Both the integration results 812 and the RRV power spectrum 814 can be displayed.

Figure 9:
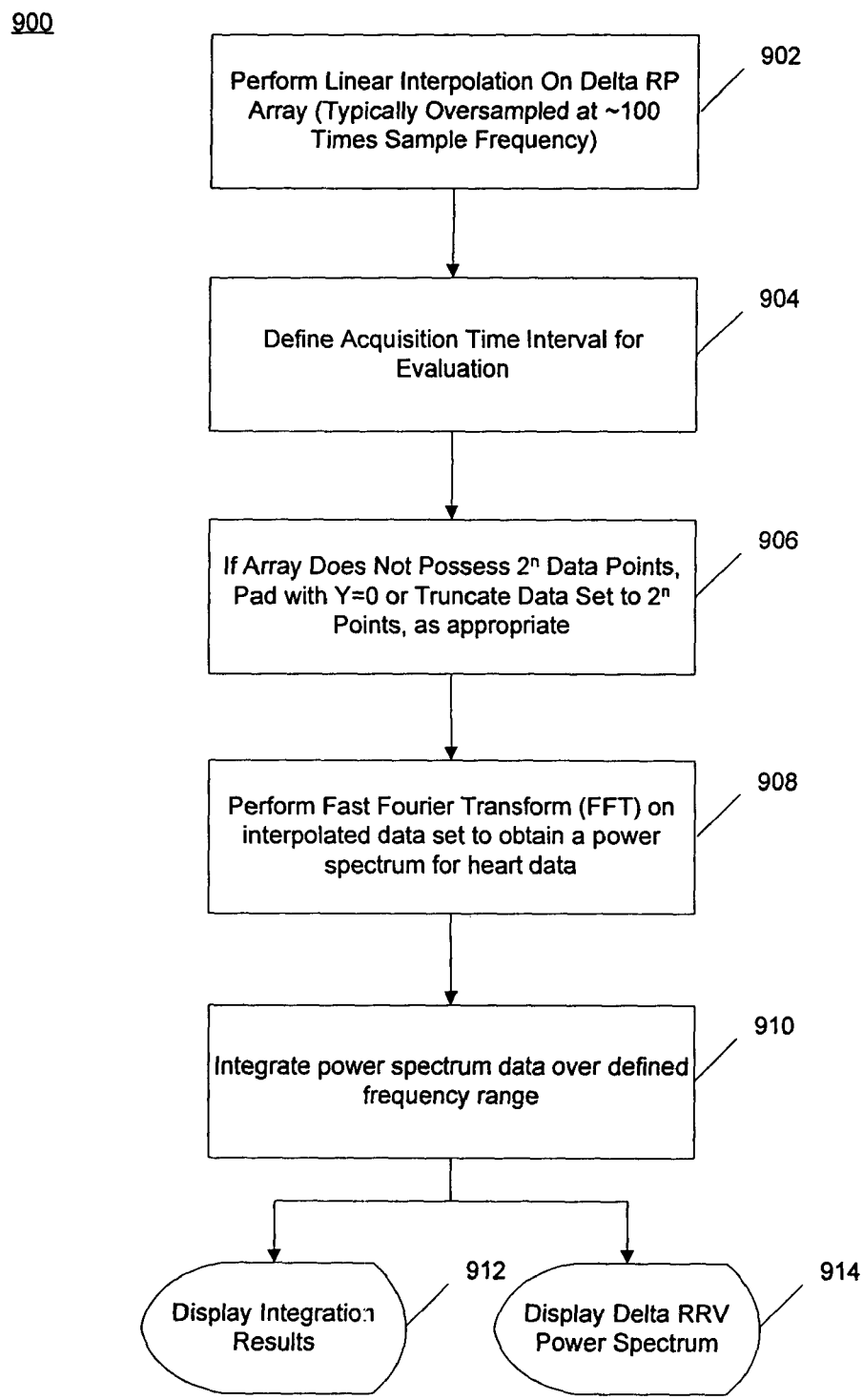
FIG. 9 is a data flow diagram of the delta respiration rate variability (ΔRRV) evaluation process.

FIG. 9 is a data flow diagram of the delta respiration rate variability (ΔRRV) evaluation process 900. This process uses as its input data the ΔRP array recorded by box 712 of FIG. 7. The steps for ΔRRV evaluation are identical to those for RRV evaluation shown in FIG. 8. The difference is in the input data set. Using the ΔRP array provides an analyst with new and valuable additional clinical data that can be examined and interpreted.

It is to be understood that the present invention illustrated herein is readily implementable by those of ordinary skill in the art as a computer program product having a medium with computer program(s) embodied thereon. The computer program product is capable of being loaded and executed on the appropriate computer processing device(s) in order to carry out the method or process steps described. Appropriate computer program code in combination with hardware implements many of the elements of the present invention. This computer code is typically stored on removable storage media. This removable storage media includes, but is not limited to, a diskette, standard CD, pocket CD, zip disk, or mini zip disk. Additionally, the computer program code can be transferred to the appropriate hardware over some type of data network.

The present invention has been described, in part, with reference to flowcharts or logic flow diagrams. It will be understood that each block of the flowchart diagrams or logic flow diagrams, and combinations of blocks in the flowchart diagrams or logic flow diagrams, can be implemented by computer program instructions.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks or logic flow diagrams.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart blocks or logic flow diagrams. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart blocks or logic flow diagrams.

Accordingly, block(s) of flowchart diagrams and/or logic flow diagrams support combinations of means for performing the specified functions, combinations of steps for performing the specified functions and program instruction means for performing the specified functions. It will also be understood that each block of flowchart diagrams and/or logic flow diagrams, and combinations of blocks in flowchart diagrams and/or logic flow diagrams can be implemented by special purpose hardware-based computer systems that perform the specified functions or steps, or combinations of special purpose hardware and computer instructions.

In the following claims, any means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. A non-invasive health monitor device for physiological monitoring of body motion to obtain a measure of variability comprising:
    a processor;
    a processor readable storage medium;
    code recorded in the processor readable storage medium to create a first array of body motion events based on discretely recorded body motions in which each element of the first array is representative of a time when a body motion event took place;
    code recorded in the processor readable storage medium to create a body motion period interval array in which each element is a body motion interval representative of the difference between successive elements of the first array of body motion events;
    code recorded in the processor readable storage medium to create a delta body motion period interval array in which each element is a delta body motion period interval representative of the difference between successive elements of the body motion period interval array;
    code recorded in the processor readable storage medium to perform a fast fourier transform (FFT) to obtain power spectrum data representative of the delta body motion period interval array; and
    code recorded in the processor readable storage medium to integrate the power spectrum data over frequency ranges of interest to obtain discrete power values for said frequency ranges of interest.

2. A non-invasive health monitor device to assist in cardiac evaluation comprising:
    a processor;
    a processor readable storage medium;
    code recorded in the processor readable storage medium to create a first array of heart vibrations based on discretely recorded heartbeats in which each element of the first array is representative of a time when a heartbeat took place;
    code recorded in the processor readable storage medium to create a heart period array in which each element is a heart period interval representative of the difference between successive heartbeats of the first array of heart vibrations;
    code recorded in the processor readable storage medium to create a delta heart period interval array in which each element is a delta heart period interval representative of the difference between successive elements of the heart period interval array;
    code recorded in the processor readable storage medium to perform a fast fourier transform (FFT) to obtain power spectrum data representative of the delta heart period interval array; and
    code recorded in the processor readable storage medium to integrate the power spectrum data over one or more frequency ranges of interest to obtain discrete power values for said one or more frequency ranges of interest.

3. The non-invasive health monitor device of claim 2 wherein the frequency ranges of interest include a low frequency (LF) range, a high frequency (HF) range, and a very high frequency (VHF) range.

4. The non-invasive health monitor device of claim 3 further comprising:
    code recorded in the processor readable storage medium to calculate a total power, TP, value that is the sum of the LF, HF, and VHF power values.

5. The non-invasive health monitor device of claim 4 further comprising:
    code recorded in the processor readable storage medium to calculate a normalized LF power value that is equal to LF/TP.

6. The non-invasive health monitor device of claim 4 further comprising:
   code recorded in the processor readable storage medium to calculate a normalized HF power value that is equal to HF/TP.

7. The non-invasive health monitor device of claim 4 further comprising:
   code recorded in the processor readable storage medium to calculate a normalized VHF power value that is equal to VHF/TP.

8. The non-invasive health monitor device of claim 3 further comprising:
   code recorded in the processor readable storage medium to calculate a power ratio value that is equal to LF/HF.

9. The non-invasive health monitor device of claim 3 wherein the LF range is approximately 0.04 to 0.15 Hz.

10. The non-invasive health monitor device of claim 3 wherein the HF range is approximately 0.15 to 0.4 Hz.

11. The non-invasive health monitor device of claim 3 wherein the VHF range is approximately 0.4 to 1.0 Hz.

12. A non-invasive health monitor device to assist in respiration evaluation comprising:
   a processor;
   a processor readable storage medium;
   code recorded in the processor readable storage medium to create a first array of respiration events based on discretely recorded body motions in which each element of the first array is representative of a time when a respiration event took place;
   code recorded in the processor readable storage medium to create a respiration period interval array in which each element is a respiration period interval representative of the difference between successive elements of the first array of respiration events;
   code recorded in the processor readable storage medium to create a delta respiration period interval array in which each element is a delta respiration period interval representative of the difference between successive elements of the respiration period interval array;
   code recorded in the processor readable storage medium to perform a fast fourier transform (FFT) to obtain power spectrum data representative of the delta respiration period interval array; and
   code recorded in the processor readable storage medium to integrate the power spectrum data over a defined range of interest to obtain a discrete power value.

13. A non-invasive health monitor device to assist in cardiac evaluation comprising:
   a processor;
   a processor readable storage medium;
   code recorded in the processor readable storage medium to create an array of first heart vibrations based on discretely recorded heartbeats in which each element of the first array is representative of a time when a first heart vibration of a heartbeat took place;
   code recorded in the processor readable storage medium to create an array of second heart vibrations having an element to element association with the array of first heart vibration, said array of second heart vibrations representative of a time when a second heart vibration of a heartbeat took place;
   code recorded in the processor readable storage medium to create a ventricular systole interval array in which each element is an interval representative of the time difference between the second and first heart vibrations of each heartbeat in the second and first heart vibration arrays;
   code recorded in the processor readable storage medium to create a delta ventricular systole interval array in which each element is a delta ventricular systole interval representative of the difference between successive elements of the ventricular systole interval array;
   code recorded in the processor readable storage medium to perform a fast fourier transform (FFT) to obtain power spectrum data representative of the delta ventricular systole interval array; and
   code recorded in the processor readable storage medium to integrate the power spectrum data over one or more frequency ranges of interest to obtain discrete power values for said one or more frequency ranges of interest.

14. The non-invasive health monitor device of claim 13 wherein the power spectrum frequency ranges of interest include a low frequency (LF) range, a high frequency (HF) range, and a very high frequency (VHF) range.

15. The non-invasive health monitor device of claim 14 further comprising:
   code recorded in the processor readable storage medium to calculate a total power, TP, value that is the sum of the LF, HF, and VHF power values.

16. The non-invasive health monitor device of claim 15 further comprising:
   code recorded in the processor readable storage medium to calculate a normalized LF power value that is equal to LF/TP.

17. The non-invasive health monitor device of claim 15 further comprising:
   code recorded in the processor readable storage medium to calculate a normalized HF power value that is equal to HF/TP.

18. The non-invasive health monitor device of claim 15 further comprising:
   code recorded in the processor readable storage medium to calculate a normalized VHF power value that is equal to VHF/TP.

19. The non-invasive health monitor device of claim 14 further comprising:
   code recorded in the processor readable storage medium to calculate a power ratio value that is equal to LF/HF.

20. The non-invasive health monitor device of claim 14 wherein the LF range is approximately 0 to 0.15 Hz.

21. The non-invasive health monitor device of claim 14 wherein the HF range is approximately 0.15 to 0.4 Hz.

22. The non-invasive health monitor device of claim 14 wherein the VHF range is approximately 0.4 to 1.0 Hz.

23. A non-invasive health monitor device for physiological monitoring of body motion to obtain a measure of variability comprising:
   a processor;
   a processor readable storage medium;
   code recorded in the processor readable storage medium to create a first array of body motion events on discretely recorded body motions in which each element of the first array is representative of a time when a body motion event took place;
   code recorded in the processor readable storage medium to create a body motion period interval array in which each element is a body motion interval representative of the difference between successive elements of the first array of body motion events;
   code recorded in the processor readable storage medium to create a delta body motion period interval array in which each element is a delta body, motion period interval representative of the difference between non-successive elements of the body motion period interval array;

code recorded in the processor readable storage medium to perform a fast fourier transform (FFT) to obtain power spectrum data representative of the delta body motion period interval array; and code recorded in the processor readable storage medium to integrate the power spectrum data over frequency ranges of interest to obtain discrete power values for said frequency ranges of interest.

* * * * *